US010119921B2

United States Patent
Takeda et al.

(10) Patent No.: US 10,119,921 B2
(45) Date of Patent: Nov. 6, 2018

(54) INTERNAL CRACK DETECTING METHOD AND INTERNAL CRACK DETECTING APPARATUS

(71) Applicant: DISCO CORPORATION, Tokyo (JP)

(72) Inventors: Noboru Takeda, Tokyo (JP); Hiroshi Morikazu, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 15/629,228

(22) Filed: Jun. 21, 2017

(65) Prior Publication Data

US 2017/0370856 A1 Dec. 28, 2017

(30) Foreign Application Priority Data

Jun. 27, 2016 (JP) ................. 2016-126204

(51) Int. Cl.
  *G01N 21/95* (2006.01)
  *G01N 21/3563* (2014.01)
  *H01L 21/66* (2006.01)

(52) U.S. Cl.
  CPC ..... *G01N 21/9505* (2013.01); *G01N 21/3563* (2013.01); *H01L 22/12* (2013.01); *G01B 2210/50* (2013.01); *G01N 21/9501* (2013.01); *G01N 2021/3568* (2013.01)

(58) Field of Classification Search
  CPC . G01N 21/9505; G01N 21/3563; H01L 22/12
  See application file for complete search history.

(56) References Cited

U.S. PATENT DOCUMENTS

| | | | | |
|---|---|---|---|---|
| 4,820,897 A | * | 4/1989 | Lefevre | H03H 3/02 219/121.61 |
| 2003/0202178 A1 | * | 10/2003 | Tsuji | G01N 21/9503 356/237.2 |
| 2006/0278831 A1 | * | 12/2006 | Matsumoto | G01N 21/59 250/341.1 |
| 2011/0025838 A1 | * | 2/2011 | Ninomiya | G01N 21/9501 348/87 |

FOREIGN PATENT DOCUMENTS

| | | |
|---|---|---|
| JP | 2010-123823 | 6/2010 |
| JP | 2011-033383 | 2/2011 |

\* cited by examiner

*Primary Examiner* — Hugh H Maupin
(74) *Attorney, Agent, or Firm* — Greer Burns & Crain, Ltd.

(57) ABSTRACT

A method for detecting an internal crack in a wafer includes a first image recording step of applying near infrared light having a transmission wavelength to a reference wafer having the same configuration as a target wafer to be subjected to the detection of the internal crack, thereby obtaining a first image of the reference wafer having no internal crack and then recording the first image, a processing step of processing the target wafer, a second image recording step of applying the near infrared light to the target wafer, thereby obtaining a second image of the processed target wafer and then recording the second image, and an internal crack detecting step of removing the same image information between the first image and the second image from the second image to obtain a residual image, thereby detecting the residual image as the internal crack in the target wafer.

15 Claims, 6 Drawing Sheets

INTERNAL CRACK DETECTING METHOD AND INTERNAL CRACK DETECTING APPARATUS

BACKGROUND OF THE INVENTION

Field of the Invention

The present invention relates to a method and apparatus for detecting an internal crack generated in processing a workpiece.

Description of the Related Art

A plurality of devices such as integrated circuits (ICs) and large-scale integrations (LSIs) are formed on the front side of a substrate so as to be separated by a plurality of crossing division lines, thus forming a wafer having the plural devices on the front side. The back side of this wafer is ground by a grinding apparatus to reduce the thickness of the wafer. Thereafter, the wafer is divided along the division lines into individual device chips by using a dicing apparatus (see Japanese Patent Laid-open No. 2010-123823, for example) or a laser processing apparatus (see Japanese Patent Laid-open No. 2011-033383, for example). The device chips thus obtained are used in electrical equipment such as mobile phones and personal computers.

In the step of stacking a plurality of circuits on the front side of the substrate, there is a case that cracks may be generated in the wafer due to internal stress such as thermal stress. Further, there is a problem such that the cracks may be left in the wafer after performing a grinding step, causing a reduction in quality of the devices. It is desired to detect whether or not the cracks are left at the time the back grinding of the wafer has been finished.

SUMMARY OF THE INVENTION

In particular, the above desire is strong in processing a wafer having a plurality of surface acoustic wave (SAW) devices formed on the front side of a lithium tantalate ($LiTaO_3$) substrate (which will be hereinafter referred to as "LT substrate") or a lithium niobate ($LiNbO_3$) substrate (which will be hereinafter referred to as "LN substrate"), and a detecting method for such a wafer has been examined.

As a method of detecting cracks generated in the LT substrate or LN substrate, it is considered to apply green or red visible light having a transmission wavelength of 500 to 700 nm to the substrate, to the back side of the substrate, thereby imaging the substrate by using imaging means to detect the cracks. In this method, the visible light applied to the back side of the substrate does not reach the devices formed on the front side of the substrate, so that the cracks generated in the substrate can be imaged. However, any roughness such as tearing generated on the back side of the substrate in the back grinding step is also imaged. Accordingly, it is difficult to clearly detect the cracks generated in the substrate.

It is therefore an object of the present invention to provide an internal crack detecting method which can clearly detect the cracks generated in a workpiece.

It is another object of the present invention to provide an internal crack detecting apparatus for performing the internal crack detecting method.

In accordance with an aspect of the present invention, there is provided an internal crack detecting method for detecting an internal crack in a wafer having a plurality of devices formed on the front side so as to be separated by a plurality of crossing division lines, the internal crack detecting method including a first image recording step of applying near infrared light having a transmission wavelength to a reference wafer having the same configuration as that of the wafer as a target wafer to be subjected to the detection of the internal crack, thereby obtaining a first image of the reference wafer having no internal crack and then recording the first image; a processing step of processing the target wafer after performing the first image recording step; a second image recording step of applying the near infrared light to the target wafer after performing the processing step, thereby obtaining a second image of the target wafer processed and then recording the second image; and an internal crack detecting step of removing the same image information between the first image and the second image from the second image to obtain a residual image after performing the second image recording step, thereby detecting the residual image as the internal crack in the target wafer.

Preferably, the processing step includes a grinding step of grinding the back side of the target wafer to reduce the thickness of the target wafer. Preferably, the target wafer includes a wafer composed of a substrate formed of lithium tantalate or lithium niobate and a plurality of SAW devices formed on the front side of the substrate, the SAW devices being separated by the division lines; and the wavelength of the near infrared light is set to 1000 to 1500 nm.

In accordance with another aspect of the present invention, there is provided an internal crack detecting apparatus including a table for holding a wafer; imaging means for applying near infrared light having a transmission wavelength to the wafer to thereby image the wafer; display means for displaying an image obtained by the imaging means; and control means for receiving the image from the imaging means and transmitting the image to the display means; the control means including a first image recording section for obtaining a first image of a reference wafer having no internal crack by using the imaging means, the reference wafer having the same configuration as that of a target wafer to be subjected to the detection of an internal crack, and for recording the first image obtained above; a second image recording section for obtaining a second image of the target wafer having the internal crack by using the imaging means, and for recording the second image obtained above; and a determining section for removing the same image information between the first image recorded in the first image recording section and the second image recorded in the second image recording section to obtain a residual image, and then determining the residual image as the internal crack.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
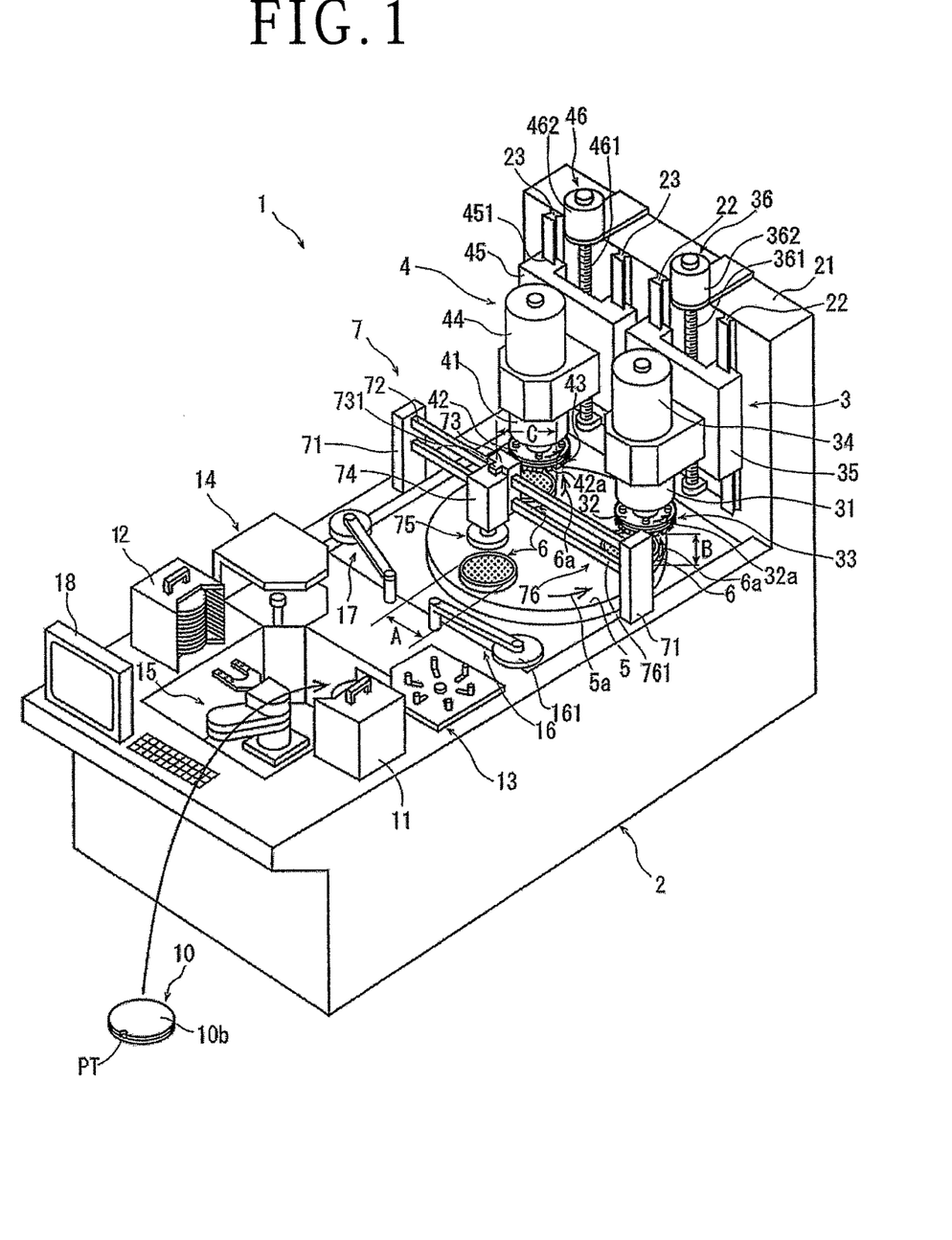
FIG. 1 is a general perspective view of a grinding apparatus including an internal crack detecting apparatus for performing an internal crack detecting method according to a preferred embodiment of the present invention.

A preferred embodiment of the internal crack detecting method according to the present invention and the detecting apparatus for performing the detecting method will now be described in detail with reference to the attached drawings. FIG. 1 is a general perspective view of a grinding apparatus 1 including the internal crack detecting apparatus for performing the internal crack detecting method according to the present invention.

The grinding apparatus 1 shown in FIG. 1 includes a substantially boxlike base housing 2. A stationary support plate 21 projects upward from the upper surface of the base housing 2 at its rear end (at a right upper end as viewed in FIG. 1). Two pairs of guide rails 22, 22 and 23, 23 are provided on the front surface of the stationary support plate 21 so as to extend in a vertical direction. A coarse grinding unit 3 as coarse grinding means is vertically movably mounted on the pair of guide rails 22, 22, and a finish grinding unit 4 as finish grinding means is vertically movably mounted on the pair of guide rails 23, 23.

The coarse grinding unit 3 includes a unit housing 31, a wheel mount 32 rotatably mounted to the lower end of the unit housing 31, a coarse grinding wheel 33 mounted on the lower surface of the wheel mount 32, an electric motor 34 mounted to the upper end of the unit housing 31 for rotating the wheel mount 32 in the direction shown by an arrow 32a, and a movable base 35 on which the unit housing 31 is mounted.

The movable base 35 is supported to the stationary support plate 21 so as to be vertically movable along the guide rails 22, 22 provided on the stationary support plate 21. The movable base 35 is provided with feeding means 36 for feeding the coarse grinding wheel 33. The feeding means 36 includes an externally threaded rod 361 rotatably supported to the stationary support plate 21 so as to extend vertically and a pulse motor 362 for rotating the externally threaded rod 361. The externally threaded rod 361 is engaged with a nut portion formed on the movable base 35. Accordingly, when the pulse motor 362 is operated to rotate the externally threaded rod 362 normally or reversely, the coarse grinding unit 3 is moved vertically (in a direction perpendicular to a holding surface of a chuck table to be hereinafter described).

The finish grinding unit 4 is similar in configuration to the coarse grinding unit 3. That is, the finish grinding unit 4 includes a unit housing 41, a wheel mount 42 rotatably mounted to the lower end of the unit housing 41, a finish grinding wheel 43 mounted on the lower surface of the wheel mount 42, an electric motor 44 mounted to the upper end of the unit housing 41 for rotating the wheel mount 42 in the direction shown by an arrow 42a, and a movable base 45 on which the unit housing 41 is mounted.

The movable base 45 is supported to the stationary support plate 21 so as to be vertically movable along the guide rails 23, 23 provided on the stationary support plate 21. The movable base 45 is provided with feeding means 46 for feeding the finish grinding wheel 43. The feeding means 46 includes an externally threaded rod 461 rotatably supported to the stationary support plate 21 so as to extend vertically and a pulse motor 462 for rotating the externally threaded rod 461. The externally threaded rod 461 is engaged with a nut portion formed on the movable base 45. Accordingly, when the pulse motor 462 is operated to rotate the externally threaded rod 461 normally or reversely, the finish grinding unit 4 is moved vertically (in the direction perpendicular to the holding surface of the chuck table).

The grinding apparatus 1 includes a turn table 5 located on the front side of the stationary support plate 21 and having an upper surface substantially flush with the upper surface of the base housing 2. The turn table 5 is a disk-shaped member having a relatively large diameter, and it is suitably rotated in the direction shown by an arrow 5a by a rotational drive mechanism (not shown). In the preferred embodiment, three chuck tables 6 are provided on the turn table 5 so as to be equally spaced at angular intervals of 120 degrees. Each chuck table 6 is rotatable about its axis in a horizontal plane and it functions as a table for holding a wafer under suction. That is, each chuck table 6 is rotated in the direction shown by an arrow 6a by a rotational drive mechanism (not shown) in performing a grinding operation. By suitably rotating the turn table 5, each chuck table 6 provided on the turn table 5 is moved to selectively take a standby position (load/unload position) A, a coarse grinding position B, and a finish grinding position C. That is, the chuck table 6 set at the standby position A is moved through the coarse grinding position B to the finish grinding position C and then returned to the standby position A by the rotation of the turn table 5.

The grinding apparatus 1 further includes a first cassette 11 located on one side (right side) with respect to the standby position A for storing a plurality of semiconductor wafers as workpieces before grinding, a second cassette 12 located on the other side (left side) with respect to the standby position A for storing the semiconductor wafers after grinding, centering means 13 located between the first cassette 11 and the standby position A for centering each semiconductor wafer before grinding, spinner cleaning means 14 located between the standby position A and the second cassette 12 for cleaning each semiconductor wafer after grinding, and handling means 15 for taking one of the plural semiconductor wafers out of the first cassette 11 and then transferring the semiconductor wafer to the centering means 13 before grinding and also for transferring the semiconductor wafer from the spinner cleaning means 14 to the second cassette 12 after grinding.

The grinding apparatus 1 further includes first transfer means 16 for transferring the semiconductor wafer from the centering means 13 to the chuck table 6 set at the standby position A before grinding and second transfer means 17 for transferring the semiconductor wafer from the chuck table 6 set at the standby position A to the spinner cleaning means 14 after grinding. Each the first transfer means 16 and the second transfer means 17 includes an arm adapted to be horizontally rotated and vertically moved and a suction pad mounted at the front end of the arm, and the arm and the suction pad are operated by a suction mechanism and a moving mechanism (both not shown).

The grinding apparatus 1 further includes an internal crack detecting apparatus 7 for imaging the semiconductor wafer held on the holding surface of the chuck table 6 set at the standby position A and detecting an internal crack generated in the semiconductor wafer. The internal crack detecting apparatus 7 includes a pair of vertically extending support members 71, 71 provided on the opposite side portions of the base housing 2 so as to be opposed to each other with the standby position A interposed therebetween.

A horizontally extending guide rod 72 is fixed at its opposite ends to the pair of support members 71, 71. The guide rod 72 has a rectangular cross section and functions as a movement guiding member. A slide block 73 is slidably mounted on the guide rod 72. More specifically, the slide block 73 has a sectionally rectangular through hole adapted to engage with the guide rod 72. That is, the guide rod 72 is inserted through the through hole of the slide block 73, whereby the slide block 73 is slidably supported to the guide rod 72.

A guide rail 731 is formed on the front surface of the slide block 73 so as to extend vertically, and imaging means 74 is provided on the slide block 73 so as to be movable along the guide rail 731. An imaging section 75 is mounted on the lower surface of the imaging means 74. The imaging section 75 functions to image the semiconductor wafer held on the holding surface (upper surface) of the chuck table 6 set at the standby position A. The imaging means 74 has a guided groove for engaging the guide rail 731, and the guided groove is engaged with the guide rail 731 to thereby vertically movably support the imaging means 74 to the slide block 73. An operation panel to be operated by an operator of the grinding apparatus 1 is provided on the upper surface of the base housing 2 at its front end portion, and display means 18 for displaying an image obtained by the imaging means 74 is provided in the vicinity of this operation panel (at the left lower end of the base housing 2 as viewed in FIG. 1).

The internal crack detecting apparatus 7 further includes moving means 76 for moving the slide block 73 supporting the imaging means 74 along the guide rail 72. The moving means 76 is composed of a linear rail 761 extending between the pair of support members 71, 71 and a movable coil (not shown) built in the slide block 73 so as to be movably mounted around the linear rail 761. For example, the linear rail 761 is configured by linearly arranging a plurality of prismatic permanent magnets so that the N poles and the S poles are alternately connected, and the plural prismatic permanent magnets linearly arranged are accommodated in a sectionally rectangular case formed of a nonmagnetic material such as stainless steel.

Thus, the linear rail 761 and the movable coil built in the slide block 73 constitute the moving means 76, which functions as a so-called shaft motor. When an electric current is applied to pass through the movable coil, a magnetic attraction force and a magnetic repulsion force are repeatedly applied to the movable coil by the operation of the linear rail 761, thereby generating a thrust force. Accordingly, by changing the direction of the electric current passing through the movable coil, the direction of movement of the slide block 73 along the linear rail 761 can be changed. While the moving means 76 is configured by a shaft motor as mentioned above in the preferred embodiment, a ball screw mechanism may be used in place of the shaft motor, for example. That is, the moving means for moving the slide block 73 along the guide rail 72 is not limited to a shaft motor in the present invention.

Figure 2:
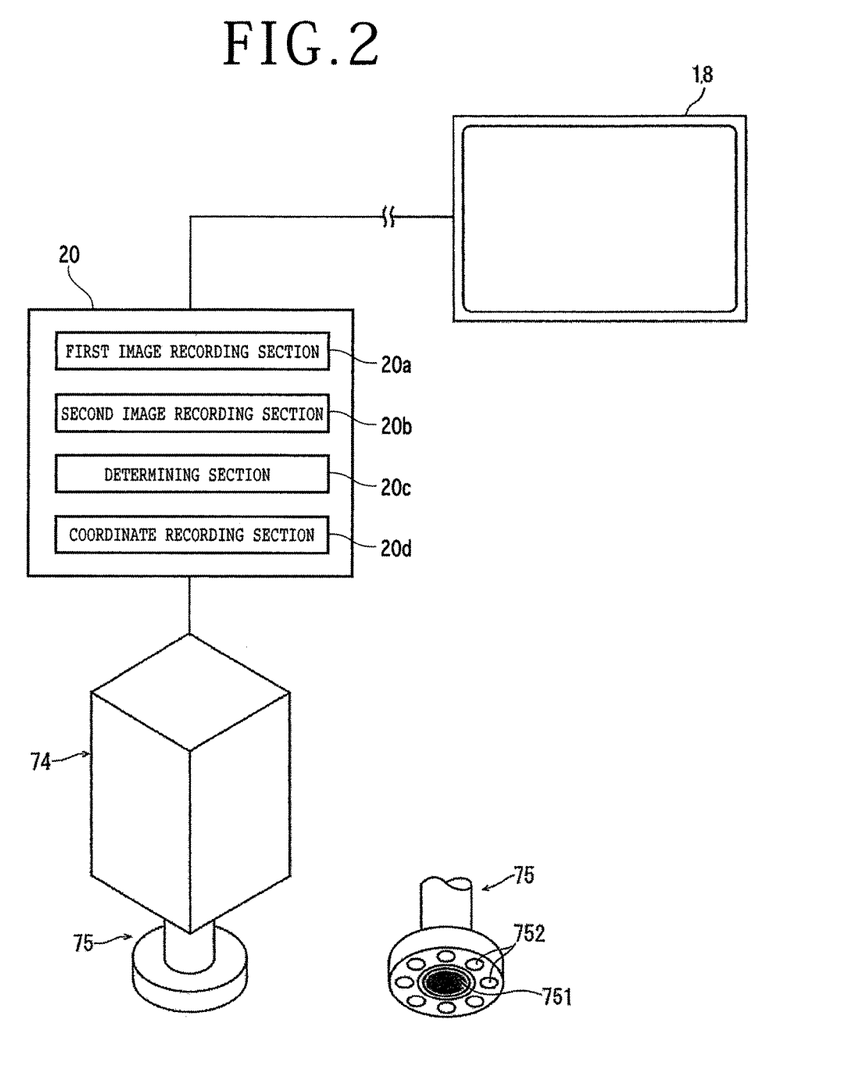
FIG. 2 is a schematic diagram showing the configuration of the internal crack detecting apparatus.

The imaging means 74 will now be described in more detail with reference to FIG. 2. As shown in FIG. 2, the imaging section 75 supported to the lower surface of the imaging means 74 includes an imaging lens 751 for imaging a target set therebelow and near infrared light applying means 752 for applying near infrared light to the target set below the imaging lens 751. In the preferred embodiment, the near infrared light applying means 752 is configured by a light emitting diode (LED) light for applying near infrared light having a wavelength of 1000 nm.

Image information obtained by the imaging means 74 is transmitted to control means 20 included in the grinding apparatus 1. This image information is also transmitted through the control means 20 to the display means 18 and then displayed by the display means 18. The control means 20 is configured by a computer, which includes a central processing unit (CPU) for performing operational processing in accordance with a control program, a read only memory (ROM) previously storing the control program, a readable and writable random access memory (RAM) for storing detected information, operation results, etc., an input interface, and an output interface. As shown in FIG. 2, the control means 20 further includes a first image recording section 20a for recording a first image to be hereinafter described, a second image recording section 20b for recording a second image obtained by imaging the wafer from the back side thereof after processing (grinding), a determining section 20c for removing the same image information between the first image recorded by the first image recording section 20a and the second image recorded by the second image recording section 20b from the second image to obtain a residual image and then determining the residual image as an internal crack generated in the wafer processed, and a coordinate recording section 20d for recording the coordinates indicating the position of the internal crack on the wafer. The first image recording section 20a, the second image recording section 20b, and the coordinate recording section 20d are defined as memory areas in the random access memory (RAM). The determining section 20c for determining the internal crack is previously stored as a program in the read only memory (ROM). The control means 20 is included in the grinding apparatus 1 and functions to input detection signals from various sensors for use in performing the grinding operation and also to output control signals to various driving mechanisms.

There will now be described an internal crack detecting method to be performed by using the internal crack detecting apparatus 7 included in the grinding apparatus 1 mentioned above.

Figure 3:
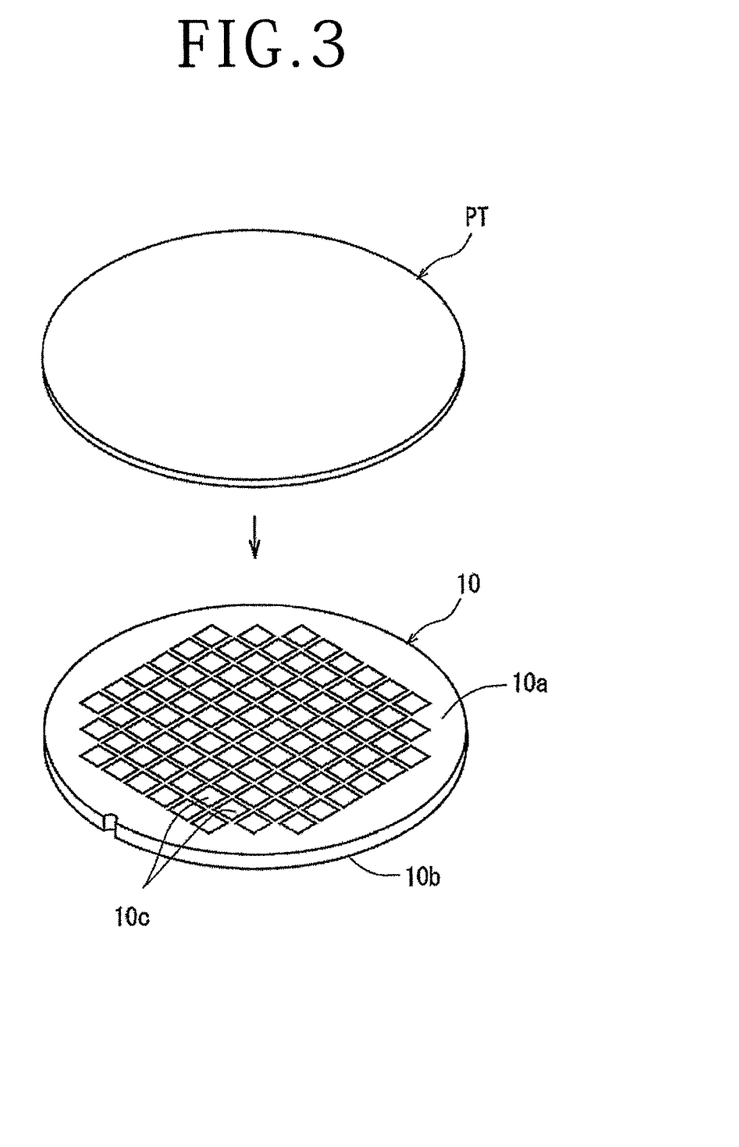
FIG. 3 is a perspective view of a wafer to be used in performing the internal crack detecting method.
Figure 4:
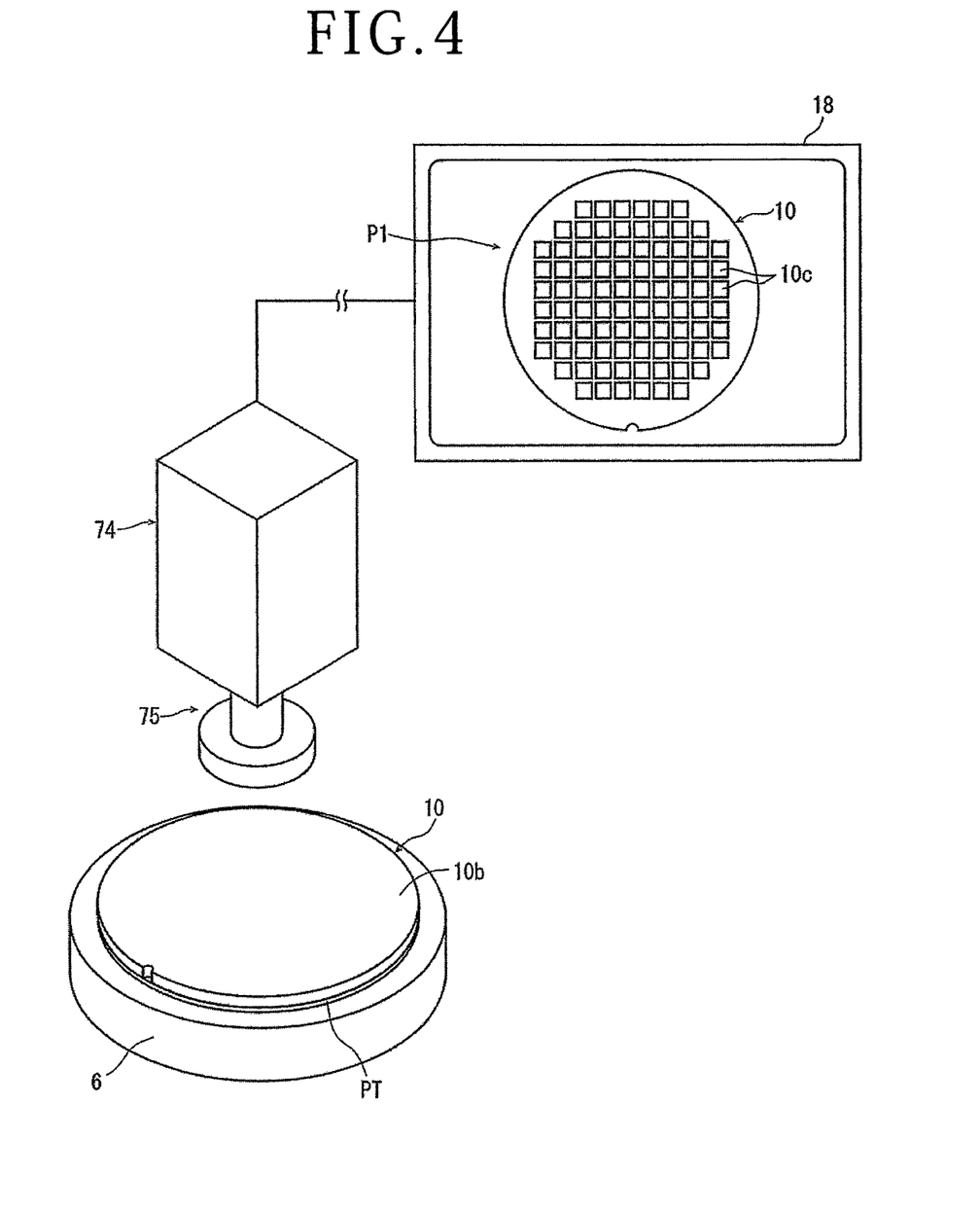
FIG. 4 is a schematic view for illustrating a first image recording step.

First, a wafer 10 to be ground is prepared as a reference wafer. The configuration of the wafer 10 is the same as that of the wafer (target wafer) to be subjected to the detection of the internal crack after grinding. More specifically, as shown in FIG. 3, the wafer 10 has a front side 10a and a back side 10b. The wafer 10 is configured by forming a plurality of SAW devices 10c on the front side of an LN substrate (on the front side 10a). A protective tape PT is attached to the front side 10a of the wafer 10. The protective tape PT is formed from a synthetic resin sheet. As shown in FIG. 1, the wafer 10 with the protective tape PT attached thereto is placed on the chuck table 6 set at the standby position A in the condition where the back side 10b of the wafer 10 before processing is oriented upward, i.e., the protective tape PT is oriented downward. Thereafter, the imaging means 74 is moved to the standby position A by the operation of the control means 20, thereby positioning the imaging section 75 directly above the wafer 10 held on the chuck table 6 set at the standby position A. Thereafter, near infrared light having a wavelength of 1000 nm is applied from the near infrared light applying means 752 to the back side 10b of the wafer 10, thereby imaging the wafer 10. Image data obtained by the imaging section 75 is transmitted to the control means 20. As described above, the image data transmitted to the control means 20 is displayed by the display means 18 and simultaneously stored into the random access memory (RAM). The near infrared light to be applied from the imaging section 75 can pass through the wafer 10 better than visible light. Accordingly, as shown in FIG. 4, the SAW devices 10c formed on the front side 10a of the wafer 10 can also be imaged.

The image of the wafer 10 to be ground stored into the random access memory (RAM) is next checked by the operator on the screen of the display means 18. If no cracks are present in the image, this image is recorded as a first image P1 into the first recording section 20a, where the first image P1 is a reference image having no internal crack. Various methods may be selected as a method of obtaining the first image P1 having no internal crack. If an internal crack is generated in forming the SAW devices 10c on the LT substrate and this internal crack is imaged, another wafer 10 to be ground may be imaged to obtain image data having no internal crack. Alternatively, even if the image of the wafer 10 includes an internal crack, image processing may be performed to remove only the internal crack from the image. Thus, the data on the internal crack is removed from the image data of the wafer 10 to prepare a reference image having no internal crack. This reference image may be used as the first image P1 and then recorded into the first image recording section 20a. In this manner, a first image recording step is performed to record the first image P1. When the imaging means 74 is not in operation, the moving means 76 is operated to move the imaging means 74 to a retracted position near one of the support members 71, 71 for supporting the linear rail 761.

After performing the first image recording step, a processing step of processing (grinding) the wafer 10 is performed. As described above, the wafer 10 to be processed is previously stored in the first cassette 11. As similar to the wafer 10 used in obtaining the first image P1 as mentioned above, the protective tape PT is attached to the front side 10a of the wafer 10 to be processed. First, the handling means 15 is operated to take one of the plural wafers 10 out of the first cassette 11 and then transfer the wafer 10 to the centering means 13. The wafer 10 placed on the centering means 13 is centered by the centering means 13. Thereafter, the first transfer means 16 is operated to transfer the wafer 10 from the centering means 13 to the chuck table 6 set at the standby position A. Thereafter, suction means (not shown) connected to the chuck table 6 is operated to hold the wafer 10 through the protective tape PT on the chuck table 6 under suction.

Figure 5A:
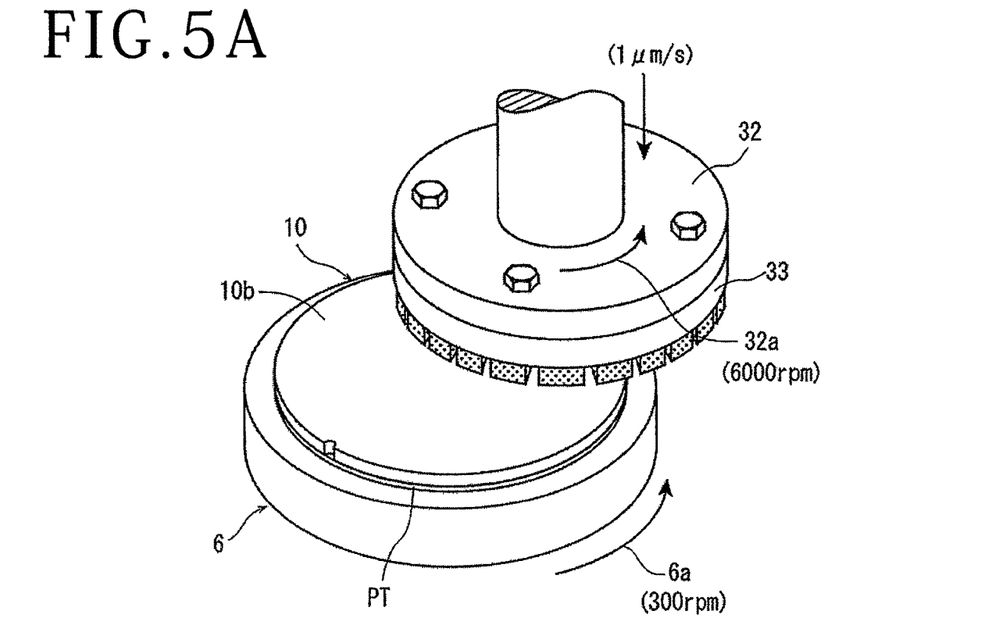
FIGS. 5A and 5B are perspective views for illustrating a grinding step as a processing step.
Figure 5B:
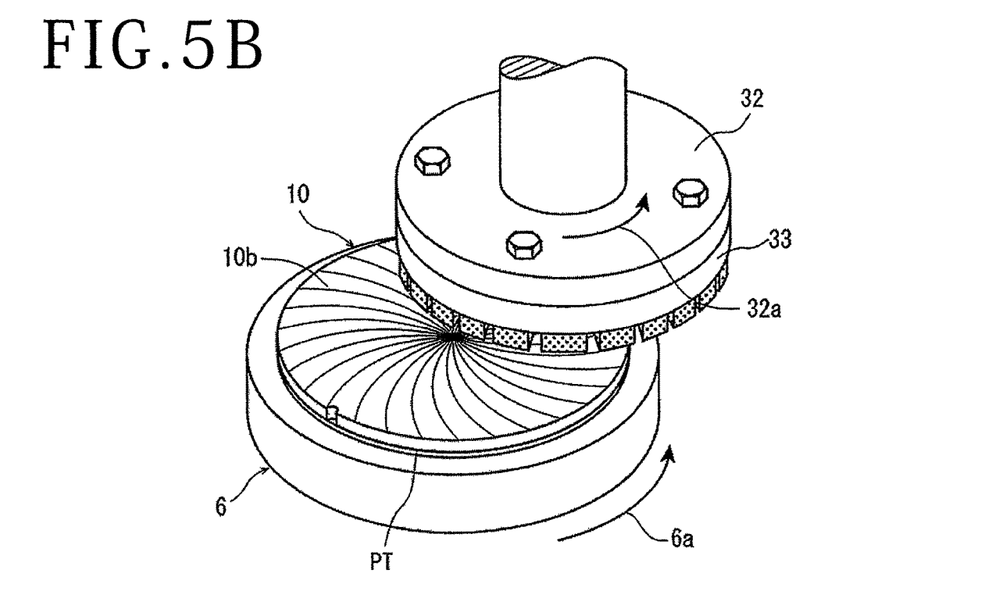

The processing step will now be further described with reference to FIG. 1 and FIGS. 5A and 5B. After holding the wafer 10 on the chuck table 6 set at the standby position A, the turn table 5 is rotated by 120 degrees in the direction of the arrow 5a by operating the rotational drive mechanism (not shown), thereby moving the chuck table 6 holding the wafer 10 to the coarse grinding position B. Thereafter, the chuck table 6 holding the wafer 10 under suction is rotated in the direction of the arrow 6a by operating the rotational drive mechanism (not shown). On the other hand, the coarse grinding wheel 33 is rotated in the direction of the arrow 32a and lowered by a predetermined amount by operating the feeding means 36 (see FIG. 5A). As a result, the back side 10b (upper surface) of the wafer 10 held on the chuck table 6 is coarse-ground by the coarse grinding wheel 33 (see FIG. 5B). When the chuck table 6 holding the wafer 10 is moved to the coarse grinding position B, another wafer 10 to be processed is held on the next chuck table 6 set at the standby position A.

After performing the coarse grinding operation as mentioned above, the turn table 5 is further rotated by 120 degrees in the direction of the arrow 5a to move the chuck table 6 holding the wafer 10 coarse-ground to the finish grinding position C and also to move the chuck table 6 holding the wafer 10 to be processed and set at the standby position A to the coarse grinding position B. Thereafter, the back side of the wafer 10 held on the chuck table 6 set at the finish grinding position C is finish-ground by the finish grinding unit 4. At the same time, the back side of the wafer 10 held on the chuck table 6 set at the coarse grinding position B is coarse-ground by the coarse grinding unit 3. The finish grinding operation to be performed by the finish grinding unit 4 is similar to the coarse grinding operation described above, and the detailed description of the finish grinding operation will therefore be omitted. After performing the finish grinding operation, the turn table 5 is further rotated by 120 degrees in the direction of the arrow 5a to move the chuck table 6 holding the wafer 10 finish-ground to the standby position A and also to move the chuck table 6 holding the wafer 10 coarse-ground to the finish grinding position C. At the same time, the chuck table 6 holding another wafer 10 to be processed is moved from the standby position A to the coarse grinding position B.

Figure 6A:
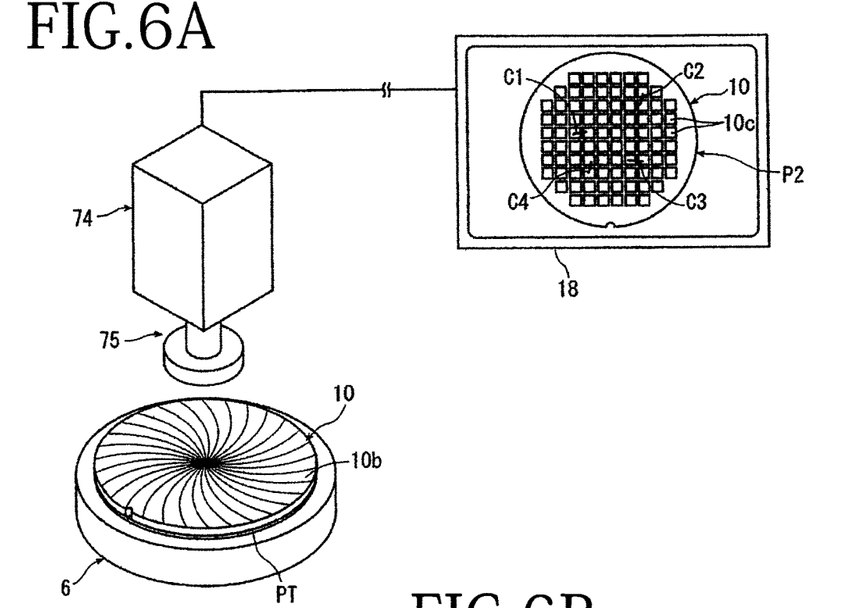
FIG. 6A is a schematic view for illustrating a second image recording step.

When the wafer 10 finish-ground is returned from the finish grinding position C to the standby position A, the moving means 76 is operated to move the imaging means 74 from the retracted position to the standby position A, thereby positioning the imaging means 74 directly above the chuck table 6 holding the wafer 10 finish-ground. Thereafter, as shown in FIG. 6A, the wafer 10 finish-ground is imaged from the back side 10b by the imaging means 74, and image data obtained by the imaging means 74 is transmitted as a second image P2 to the control means 20 and displayed through the control means 20 by the display means 18. Further, the image information on the second image P2 is recorded into the second image recording section 20b of the control means 20. As described above, the imaging means 74 is so configured as to apply near infrared light to the wafer 10 and thereby image the wafer 10. Since near infrared light can pass through the wafer 10 better than visible light, the near infrared light applied to the wafer 10 can pass through any roughness such as tearing on the back side 10b as caused by the grinding operation, so that there is no possibility that such roughness on the back side 10b may disturb the detection of internal cracks in the wafer 10. In the preferred embodiment shown in FIG. 6A, internal cracks C1 to C4 are left in the wafer 10 after forming the SAW devices 10c on the front side 10a of the wafer 10 and grinding the back side 10b of the wafer 10 as mentioned above. In this manner, a second image recording step is performed to record the second image P2.

Figure 6B:
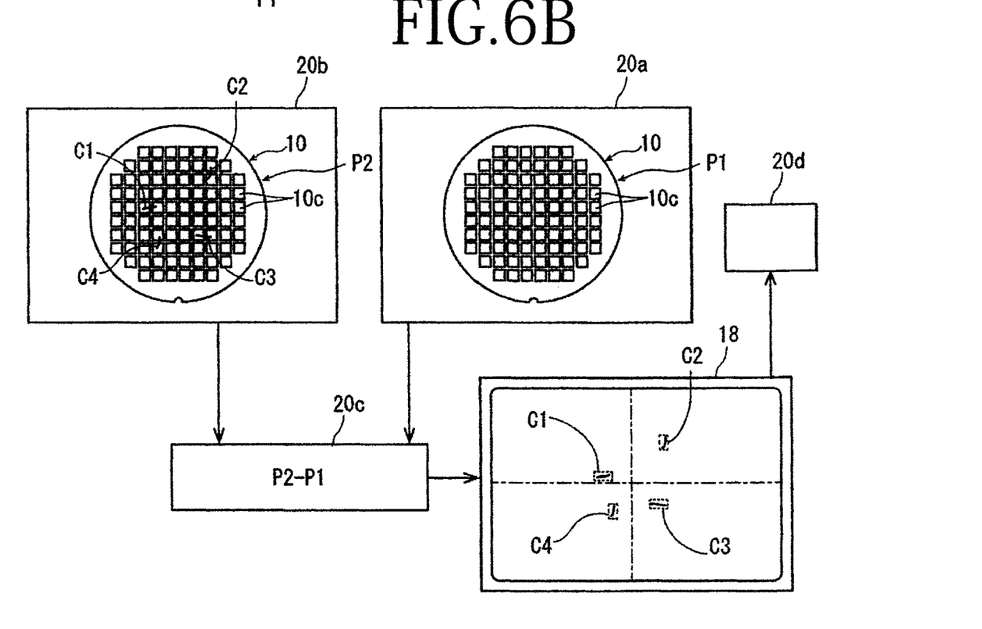
FIG. 6B is a schematic diagram for illustrating an internal crack detecting step.

After performing the second image recording step, an internal crack detecting step is performed by executing the control program constituting the determining section 20c. More specifically, as shown in FIG. 6B, the image information on the second image P2 recorded in the second image recording section 20b is read and the image information on the first image P1 recorded in the first image recording section 20a is also read. Thereafter, at the determining section 20c, the image information on the second image P2 is compared with the image information on the first image P1. Thereafter, the same image information between the first image P1 and the second image P2 is erased from the second image P2 to obtain residual image information, which is then displayed by the display means 18. In this manner, the first image P1 having no internal cracks is removed from the second image P2 having the internal cracks C1 to C4, so that only the internal cracks C1 to C4 are displayed on the screen of the display means 18 as shown in FIG. 6B. Thus, the presence or absence of the internal cracks in the wafer 10 can be clearly detected.

After performing the internal crack detecting step, it is preferable to specify the coordinate positions of the cracks C1 to C4 and then record them into the coordinate recording section 20d of the control means 20. Information on the coordinate positions thus recorded may be transferred to a dividing step of dividing the wafer 10 into the SAW devices 10c. In this case, the SAW devices 10c formed at the coordinate positions of the internal cracks can be easily identified as devices having a high possibility of causing trouble, in picking up each SAW device 10c divided from the wafer 10.

As described above, the wafer 10 finish-ground is returned to the standby position A and next imaged by using the imaging means 74 at the standby position A to detect the presence or absence of internal cracks in the wafer 10. This is merely illustrative and may be suitably modified. For example, after returning the wafer 10 finish-ground to the standby position A, the wafer 10 may be transferred from the standby position A to the spinner cleaning means 14 by operating the second transfer means 17 to clean the wafer 10 and next dry it. Thereafter, the wafer 10 thus cleaned may be returned to the standby position A and then imaged by using the imaging means 74 to obtain the second image P2. Thereafter, the wafer 10 may be directly stored into the second cassette 12. In this case, internal cracks in the wafer 10 can be detected more accurately without being hindered by any contamination on the wafer 10.

While the internal crack detecting apparatus 7 is incorporated in the grinding apparatus 1 in the above preferred embodiment, the present invention is not limited to this configuration. For example, the internal crack detecting apparatus according to the present invention may be configured as a separate detecting apparatus independent of a processing apparatus for processing any processing. Further, the processing apparatus in the present invention may be a cutting apparatus having a cutting blade for cutting a wafer as a workpiece along division lines, which are formed on the front side of the wafer to define a plurality of separate regions where devices are formed. Further, the processing apparatus in the present invention may also be a laser processing apparatus for performing laser processing to such a wafer as mentioned above. For example, a laser beam having an absorption wavelength to the wafer is applied along the division lines to perform ablation on the front side of the wafer and thereby divide the wafer along the division lines. As another example, a laser beam having a transmission wavelength to the wafer is applied along the division lines to form a modified layer inside the wafer along each division line and thereby divide the wafer along each division line where the modified layer is formed as a division start point. As still another example, a laser beam having a transmission wavelength to the wafer is applied along the division lines in the condition where the numerical aperture of a focusing lens for focusing the laser beam is suitably adjusted with respect to the refractive index of the material forming the wafer, thereby forming so-called shield tunnels arranged along each division line, each shield tunnel being composed of a fine hole extending from the front side of the wafer to the back side thereof and an amorphous region formed around the fine hole so as to shield it, and the wafer is divided along each division line where the shield tunnels are formed inside the wafer. Further, the present invention is applicable also to a processing apparatus for performing plasma etching to the front side of the wafer.

While the workpiece used in the above preferred embodiment is a wafer composed of an LT substrate and SAW devices formed on the LT substrate, the workpiece applicable in the present invention may be a wafer composed of an LN substrate and devices formed on the LN substrate. Further, the workpiece applicable in the present invention may be any workpiece capable of transmitting near infrared light.

Further, while the near infrared light applying means used in the above preferred embodiment is configured to apply near infrared light having a wavelength of 1000 nm, the wavelength of the near infrared light passing through the workpiece may be suitably selected in a generally known near infrared region. In consideration of the material, thickness, etc. of a substrate forming a general semiconductor wafer, the wavelength of the near infrared light to be applied from the near infrared light applying means in the present invention is preferably set to 1000 to 1500 nm.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. An internal crack detecting method for detecting an internal crack in a wafer having a plurality of devices formed on a front side so as to be separated by a plurality of crossing division lines, said internal crack detecting method comprising:
   a first image recording step of applying near infrared light having a transmission wavelength to a reference wafer having the same configuration as that of said wafer as a target wafer to be subjected to the detection of said internal crack, thereby obtaining a first image of said reference wafer having no internal crack and then recording said first image;
   a processing step of processing said target wafer after performing said first image recording step;
   a second image recording step of applying said near infrared light to said target wafer after performing said processing step, thereby obtaining a second image of said target wafer processed and then recording said second image; and
   an internal crack detecting step of removing the same image information between said first image and said second image from said second image to obtain a residual image after performing said second image recording step, thereby detecting said residual image as said internal crack in said target wafer.

2. The internal crack detecting method according to claim 1, wherein said processing step includes a grinding step of grinding a back side of said target wafer to reduce the thickness of said target wafer.

3. The internal crack detecting method according to claim 1, wherein said target wafer includes a wafer composed of a substrate formed of lithium tantalate or lithium niobate and a plurality of SAW devices formed on a front side of said substrate, said SAW devices being separated by said division lines; and
   the wavelength of said near infrared light is set to 1000 to 1500 nm.

4. The internal crack detecting apparatus according to claim 3, wherein if said internal crack is generated in forming the SAW devices on said substrate and said internal crack is imaged, another wafer to be ground is imaged to obtain image data having no internal crack.

5. The internal crack detecting method according to claim 1, wherein said reference wafer used during said first image recording step and said target wafer used during said second image recording step are the same wafer.

6. The internal crack detecting method according to claim 1, wherein said first image comprises an image of the entirety of said reference wafer and said second image comprises an image of the entirety of said target wafer.

7. The internal crack detecting method according to claim 6, wherein said reference wafer used during said first image recording step and said target wafer used during said second image recording step are the same wafer.

8. The internal crack detecting method according to claim 1, wherein said same image information removed during said internal crack detecting step comprises image information related to said devices and said crossing division lines.

9. The internal crack detecting method according to claim 1, further comprising a step of removing an internal crack from the first image.

10. An internal crack detecting apparatus comprising:
a table for holding a wafer;
imaging means for applying near infrared light having a transmission wavelength to said wafer to thereby image said wafer;
display means for displaying an image obtained by said imaging means; and
control means for receiving said image from said imaging means and transmitting said image to said display means;
said control means including:
a first image recording section for obtaining a first image of a reference wafer having no internal crack by using said imaging means, said reference wafer having the same configuration as that of a target wafer to be subjected to the detection of an internal crack, and for recording said first image obtained above;
a second image recording section for obtaining a second image of said target wafer having said internal crack by using said imaging means, and for recording said second image obtained above; and
a determining section for removing the same image information between said first image recorded in said first image recording section and said second image recorded in said second image recording section to obtain a residual image, and then determining said residual image as said internal crack.

11. The internal crack detecting apparatus according to claim 10, wherein said control means further includes a coordinate recording section for recording the coordinates indicating the position of said internal crack in said target wafer.

12. The internal crack detecting apparatus according to claim 10, wherein said reference wafer associated with said first image recording section and said target wafer associated with said second image recording section are the same wafer.

13. The internal crack detecting apparatus according to claim 10, wherein said first image comprises an image of the entirety of said reference wafer and said second image comprises an image of the entirety of said target wafer.

14. The internal crack detecting apparatus according to claim 13, wherein said reference wafer associated with said first image recording section and said target wafer associated with said second image recording section are the same wafer.

15. The internal crack detecting apparatus according to claim 10, wherein said same image information removed by said determining section comprises image information related to devices and crossing division lines.

* * * * *